(12) United States Patent
Isaza

(10) Patent No.: US 6,739,337 B2
(45) Date of Patent: *May 25, 2004

(54) SYSTEM AND METHOD FOR TRANSIENT RESPONSE AND ACCURACY ENHANCEMENT FOR SENSORS WITH KNOWN TRANSFER CHARACTERISTICS

(75) Inventor: Fernando J. Isaza, Carlsbad, CA (US)

(73) Assignee: Nellcor Puritan Bennett Incorporated, Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/400,958

(22) Filed: Mar. 27, 2003

(65) Prior Publication Data

US 2003/0192542 A1 Oct. 16, 2003

Related U.S. Application Data

(62) Division of application No. 09/231,145, filed on Jan. 15, 1999, now Pat. No. 6,553,991, which is a continuation of application No. 08/818,174, filed on Mar. 14, 1997, now Pat. No. 5,865,168.

(51) Int. Cl.[7] .............................................. A61M 16/00
(52) U.S. Cl. ........................... 128/204.21; 128/204.23; 128/205.23; 128/202.22
(58) Field of Search ....................... 128/204.21, 204.23, 128/205.23, 202.22

(56) References Cited

U.S. PATENT DOCUMENTS

| | | | | | |
|---|---|---|---|---|---|
| 3,802,417 | A | * | 4/1974 | Lang .......................... 600/537 |
| 3,878,724 | A | * | 4/1975 | Allen .......................... 374/169 |
| 3,929,588 | A | * | 12/1975 | Parker et al. ............. 205/782.5 |
| 4,019,382 | A | * | 4/1977 | El-Gammal ................. 600/537 |
| 4,140,106 | A | * | 2/1979 | Kirmaier ..................... 600/532 |
| 4,248,245 | A | * | 2/1981 | Kempin ....................... 600/537 |
| 4,357,936 | A | * | 11/1982 | Ellestad et al. ............. 600/537 |
| 4,638,791 | A | * | 1/1987 | Krogh et al. ........... 128/204.23 |
| 4,642,785 | A | * | 2/1987 | Packard et al. .............. 374/169 |
| 4,692,299 | A | | 9/1987 | Crew et al. |
| 4,873,655 | A | | 10/1989 | Kondraske |
| 4,965,756 | A | | 10/1990 | Pearman et al. |
| 5,207,214 | A | | 5/1993 | Romano |
| 5,249,453 | A | * | 10/1993 | Usami et al. .............. 73/23.32 |
| 5,263,369 | A | * | 11/1993 | Cutler ...................... 73/204.15 |
| 5,303,698 | A | * | 4/1994 | Tobia et al. ............ 128/204.21 |
| 5,305,727 | A | * | 4/1994 | Gopp .......................... 123/688 |
| 5,319,540 | A | | 6/1994 | Isaza et al. |
| 5,365,922 | A | * | 11/1994 | Raemer .................. 128/204.23 |
| 5,367,475 | A | | 11/1994 | White |
| 5,386,689 | A | | 2/1995 | Bozich et al. |
| 5,392,258 | A | | 2/1995 | Gabrielson et al. |
| 5,519,605 | A | | 5/1996 | Cawlfield |
| 5,569,847 | A | | 10/1996 | Hasegawa et al. |
| 5,577,496 | A | | 11/1996 | Blackwood et al. |
| 5,590,638 | A | | 1/1997 | Nishimura et al. |
| 5,600,056 | A | | 2/1997 | Hasegawa et al. |
| 5,622,164 | A | * | 4/1997 | Kilis et al. .............. 128/200.24 |
| 5,865,168 | A | * | 2/1999 | Isaza ...................... 128/200.24 |
| 6,019,879 | A | * | 2/2000 | Chu et al. ..................... 204/406 |
| 6,186,142 | B1 | * | 2/2001 | Schmidt et al. ......... 128/204.23 |
| 6,553,991 | B1 | * | 4/2003 | Isaza ...................... 128/204.21 |
| 6,575,152 | B2 | * | 6/2003 | Poggio et al. .............. 123/681 |

* cited by examiner

Primary Examiner—Aaron J. Lewis
(74) Attorney, Agent, or Firm—Fulwider Patton Lee & Utecht, LLP

(57) ABSTRACT

A parameter of interest being measured by a sensor is estimated from output response data from the sensor and the known transfer function of the sensor, allowing fast and accurate sensor data from sensors having a dynamic characteristic otherwise precluding assessment of the sensor input. A parameter of breathing gas from a ventilator is determined based upon the known transfer function and a plurality of the sensor output signals at predetermined intervals of time, to provide an estimation of the parameter of interest.

6 Claims, 1 Drawing Sheet

SYSTEM AND METHOD FOR TRANSIENT RESPONSE AND ACCURACY ENHANCEMENT FOR SENSORS WITH KNOWN TRANSFER CHARACTERISTICS

RELATED APPLICATIONS

This is a divisional of Ser. No. 09/231,145, filed Jan. 15, 1999, now U.S. Pat. No. 6,553,991, which is a continuation of Ser. No. 08/818,174 filed Mar. 14, 1997, now U.S. Pat. No. 5,865,168.

BACKGROUND OF THE INVENTION

1. Field of the Invention

This invention relates generally to enhancement of accuracy of sensor devices with known transfer functions and the use of information about the response of a sensor to an input parameter to closely estimate the input parameter, and more particularly concerns a system and method for determining a parameter of breathing gas in a patient ventilator from a sensor for the parameter, based upon a known transfer function of the sensor.

2. Description of Related Art

When a sensor is used to obtain data about a particular characteristic of the environment such as temperature, or the oxygen content of a given gas mixture, for example, the dynamic characteristics of the sensor, as well as the dynamic nature of such a parameter or variable, generally interfere with the accurate assessment of the parameter or variable of interest, unless and until a stable condition of equilibrium is reached by both the parameter or variable of interest to be sensed and the sensor.

The mathematical relationship between the output of a control system and its input is known as the transfer function. For a linear system, the transfer function is the Laplace transform of the output divided by the Laplace transform of the input under conditions of zero initial-energy storage. The dynamic characteristics exhibited by a particular sensor can usually be analyzed and described by the particular transfer function of the sensor. The transfer functions of many sensing elements are already known or easily ascertained, so that the response of the sensor to a given input can readily be determined.

For example, a thermistor typically has a dynamic characteristic such that a period of time elapses following initiation of temperature measurement by the thermistor before the voltage output from the thermistor represents an acceptably accurate reading of the temperature being measured. The graph shown in FIG. 1 illustrates the response of a typical thermistor to a step change in temperature, indicating that at least 0.4 seconds pass before the sensor reading substantially approximates the true value for the temperature.

Similarly, in measurement of flow of a gas with hot film anemometers, knowledge of the temperature of the gas being measured is essential to the estimation of flow. Conventional techniques for measurement of gas flow with hot film anemometers have not been able to eliminate the error introduced by the transient performance of the sensor when the gas temperature changes, and consequently involve waiting until transients in a temperature sensor's output are substantially gone and a steady state has been reached before relying upon a temperature reading. For applications where fast and accurate measurement of the temperature is required, enhancement of the speed and accuracy of an otherwise normally slow and unstable sensor response is desirable.

Other types of sensors also frequently have a time constant ($\tau$) for adjustment to a step change of a variable parameter being measured that can be unacceptable where fast and accurate measurements are needed. Typical oxygen sensors, for example, have a time constant in the range of 10 to 15 seconds. Clearly, an oxygen concentration measurement from such a sensor will not be accurate until at least 50 to 75 seconds have elapsed, and then the accuracy typically is not better than 2%. It would be desirable to provide a system and method that allows the use of such otherwise slow sensors to obtain accurate information (accuracy depends on the sensor's estimate of $\tau$) about the oxygen content of a gas mixture within a shorter period of time from the onset of the measurement. The present invention meets these needs.

SUMMARY OF THE INVENTION

Briefly, and in general terms, the present invention provides for a system and method that provide for the estimation of a measured parameter of interest from output response data from a sensor having a known transfer function, allowing fast and accurate sensor data from sensors having a dynamic characteristic otherwise precluding assessment of the sensor input when the measured parameter is also subject to dynamic change.

In one currently preferred embodiment, the invention accordingly provides for a system for determining parameters of a patient respiratory system for a patient receiving breathing gas from a ventilator having a source of the breathing gas and a ventilation flow path for delivering the breathing gas in fluid communication with the patient. The system comprises a sensor having a known transfer function and generating sensor output signals indicative of a parameter of interest, as well as computing means connected to the sensor for receiving a plurality of the sensor output signals at predetermined intervals of time, for processing the plurality of output signals, and for determining an estimate of the parameter of interest of the breathing gas in the ventilation flow path based upon the sensor input signals and the known transfer function. Means are preferably also provided for outputting an indication of the estimate of the parameter of interest.

The invention also provides for a method for determining parameters of a patient airway for a patient receiving breathing gas from a ventilator having a source of the breathing gas, a ventilation flow path for delivering the breathing gas in fluid communication with the patient, and a sensor having a known transfer function for generating sensor output signals indicative of a parameter of interest of the breathing gas. The method comprises the steps of generating sensor output signals indicative of the parameter of interest; determining an estimation of the parameter of interest based upon the known transfer function and a plurality of the sensor output signals at predetermined intervals of time; and outputting an indication of the estimation of the parameter of interest.

The dynamic characteristic exhibited by a particular sensor can usually be analyzed and explained through the particular transfer function of the sensor. For many sensing elements, these transfer functions are already known or easily determined, so that the response of a sensor to a given input can readily be determined, and an accurate value of an input signal can be readily determined from the transfer function of the sensor and a plurality of output responses of the sensor using the system and method of the invention.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
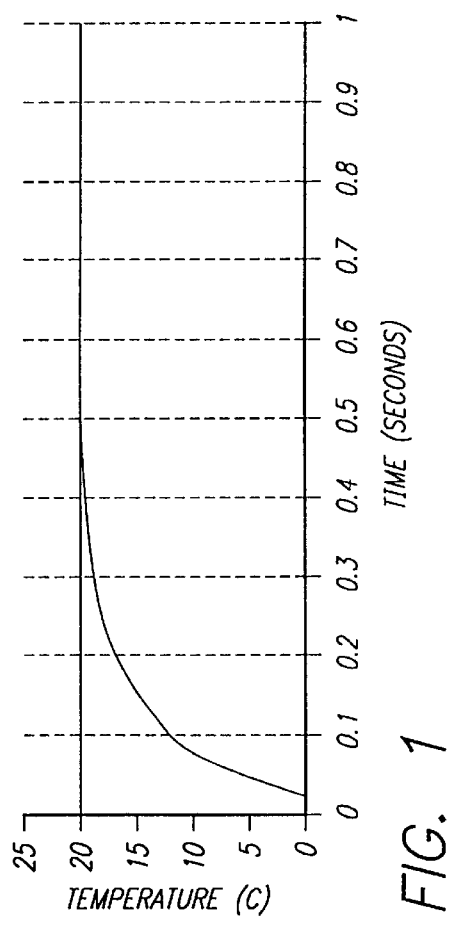
FIG. 1 is a graph illustrating the response delay of a typical thermistor to a step change in temperature.

The dynamic characteristics of a sensor and a parameter or variable being measured by the sensor can interfere with an accurate sensor measurement, generally requiring that a stable condition of the parameter of interest and the sensor be reached before the sensor measurement becomes reliably accurate. Unfortunately, when fast and accurate sensor measurements are required, the period of time required for stabilization of sensor response and a parameter value can be unacceptable, particularly when parameter values are continuously changing, precluding the possibility of accurate sensor measurements.

As is illustrated in the drawings, the invention is embodied in a system and method for estimation of an input parameter from a plurality of output responses of a sensor having a known transfer function, allowing fast and accurate sensor data from sensors having a dynamic characteristic otherwise precluding assessment of the sensor input when the measured parameter is also subject to dynamic change.

Figure 2:
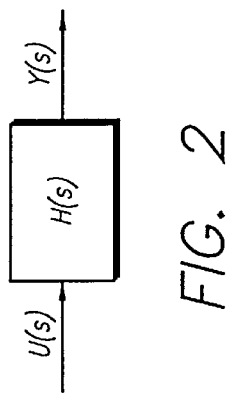
FIG. 2 is a block diagram of a typical thermistor transfer function.

A typical thermistor transfer function can be represented by the block diagram shown in FIG. 2, where U(s) represents the Laplace transformation of the input signal, H(s) represents the Laplace transformation of the transfer function, and Y(s) represents the Laplace transformation of the output signal. The representation in FIG. 2 is commonly used to describe continuous, real time systems.

From the block diagram, it is evident that:

$$Y(s)=H(s)*U(s) \qquad \text{Eq. 1}$$

A similar representation can be derived in terms of the Z transform commonly used for describing discrete time systems, giving Equation 2:

$$Y(z)=H(z)*U(z) \qquad \text{Eq. 2}$$

It is a well known and documented fact that thermistors, some oxygen sensors, and other sensing devices have the following transfer function:

$$H(s) = \frac{1}{\tau s + 1} \qquad \text{Eq. 3}$$

where $\tau$ has dimensions of time and is the sensor's time constant.

Equation 3 is also known to be the transfer function for a first order low pass filter with a cut off frequency equal to $W_0$:
in which $$W_0 = 2\pi f_0 = 1/\tau \qquad \text{Eq. 4}$$

where $f_0$ is the cut off frequency.

The transfer function of the low pass filter can also be written in terms of the Z transform, as follows:

$$H(z) = \frac{(1-\alpha) \cdot z}{z - \alpha} \qquad \text{Eq. 5}$$

Equation 5 represents the transfer function of the first order low pass filter described by the following equation:

$$Y(k)=\alpha Y(k-1)+(1-\alpha) \cdot U(k) \qquad \text{Eq. 6}$$

where U(k) is the input signal to a low pass filter at time kT; T is the sample interval time; Y(k) and Y(k−1) are the filter's response/outputs for the kT and (k−1)T times respectively.

The parameter a can be determined by the expression:

$$\alpha = 2 - \cos W_0 T - ((3 - \cos W_0 T)(1 - \cos W_0 T))^{0.5} \qquad \text{Eq. 7}$$

where T is the sample time interval to be used, and which can be 5 msec., for example.

Normally, provided the transfer function of a particular sensor is known, one is interested in determining an estimate of the output of the sensor in response to a known input signal. However, in situations where fast and accurate output responses are needed from a slow sensor, the true input signal is particularly of interest, and can be determined according to the system and method of the invention, given the known transfer function and data of the measurement outputs of the sensor device.

The invention accordingly provides for determination of an estimate of an input signal U(k) of a parameter to be measured based upon the transfer function described in Equation 6. In a preferred embodiment, the invention provides for a system and method for determination of an estimate of an input signal U(k) of a parameter to be measured in a microprocessor controlled patient ventilator to be used for measurement of flow, according to the following:

$$U(k)=(Y(k)-\alpha Y(k-1))/(1-\alpha) \qquad \text{Eq. 8}$$

where k is the control or sample interval number, which is typically 5 msec, although other similar time periods would be suitable.

Figure 3:
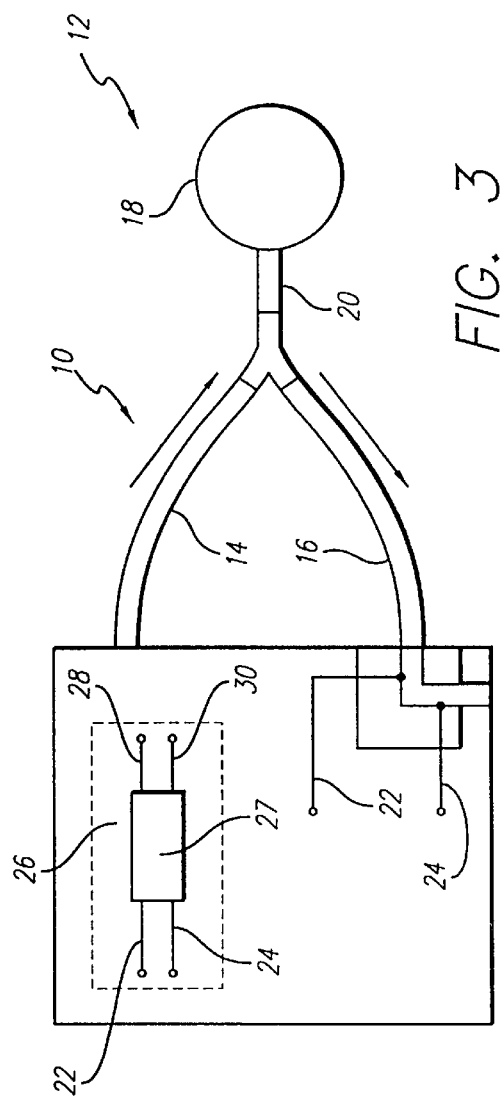
FIG. 3 is a schematic diagram of a microprocessor controlled ventilator of a patient respiratory system implementing the system and method of the invention for determining parameters of the breathing gas of the patient respiratory system.

Referring to FIG. 3, a microprocessor controlled ventilator 10 of a patient respiratory system 12 provides a source of breathing gas to a patient. The ventilator is typically connected by an inhalation line 14 and an exhalation line 16 to a patient lung 18 receiving breathing gas from the ventilation system via tubing 20. The ventilator includes a system according to the invention for determining one or more parameters of the breathing gas of the patient respiratory system, such as the temperature, flow rate, or oxygen concentration, for example. In the exemplary embodiment illustrated in FIG. 3, the ventilator includes a temperature sensor 22, such as a thermistor, for example, connected to the exhalation line for measuring the temperature of the breathing gas in the exhalation line, and a flow meter 24, such as a hot film anemometer, for example, for measuring flow in the exhalation line, although such sensors could also be provided at other locations in the patient airway as well. An oxygen concentration sensor, or other sensors, can also be provided for monitoring various parameters of the breathing gas, and preferably the transfer function for each sensor is known.

The system for determining parameters of the breathing gas of the patient respiratory system is currently preferably implemented in a microprocessor computer 26 with associated memory for storing the transfer functions of the sensors, and the microprocessor 27 is connected to the sensors for receiving the outputs of the sensors. The microprocessor computer preferably also includes a clock providing timing signals for defining sample or control time intervals T, which is currently preferably 5 msec., although other similar time intervals could also be suitable. The microprocessor receives at least a first temperature output signal $Y_t(k-1)$ at a first control time interval (k−1) and a second temperature output signal $Y_t(k)$ at a second control time interval (k), and processes the sensor output signals utilizing the transfer function for the temperature sensor stored in the microprocessor computer to determine an estimate of the temperature of the breathing gas. The ventilator system also preferably includes an output line 28 for providing an output reading of the temperature $U_t(k)$. Similarly, The microprocessor receives at least a first flow output signal $Y_f(k-1)$ at a first control time interval (k−1) and a second flow output signal $Y_f(k)$ at a second control time interval (k), and processes the flow sensor output signals utilizing the flow sensor transfer function stored in the microprocessor computer to determine an estimate of the flow $U_f(k)$ of the breathing gas. The ventilator system also preferably includes an output line 30 for providing an output reading of the flow $U_f(k)$. While this example of the system and method of the invention illustrates the use of two output data points at controlled time intervals for determining the parameter of interest to be measured by the sensor, it should be apparent that additional output data points taken at controlled time intervals can also be utilized to determine the parameter of interest utilizing the known transfer function of the sensor.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. In a system for determining a dynamically changing output parameter of interest, the system including an oxygen sensor for determining the output parameter of interest, the oxygen sensor exhibiting a dynamic characteristic having a time constant, resulting in a transient performance of the oxygen sensor, said oxygen sensor having a known transfer function and generating oxygen sensor output signals indicative of the output parameter of interest, the improvement in the system comprising:

a computing device connected to the oxygen sensor for receiving a plurality of said oxygen sensor output signals from the oxygen sensor at predetermined intervals of time, for processing said plurality of output signals, and for determining an estimate of said output parameter of interest based upon said oxygen sensor output signals and said known transfer function; and means for outputting an indication of the estimate of said output parameter of interest.

2. In a method for determining a dynamically changing parameter of interest by providing an oxygen sensor exhibiting a dynamic characteristic having a time constant, resulting in a transient performance of the sensor, said oxygen sensor having a known transfer function for determining the output parameter of interest, the improvement in the method comprising the steps of:

receiving oxygen sensor output signals from said oxygen sensor;

determining an estimation of said output parameter of interest based upon said known transfer function and a plurality of said oxygen sensor output signals at predetermined intervals of time; and outputting an indication of the estimation of said output parameter of interest.

3. A system for determining a dynamically changing output parameter of interest within a patient ventilation system, the system comprising:

an oxygen sensor exhibiting a dynamic characteristic having a time constant, resulting in a transient performance of the oxygen sensor, said oxygen sensor generating oxygen sensor output signals and having a known transfer function for determining the output parameter of interest;

computing means connected to said oxygen sensor for receiving a plurality of said oxygen sensor output signals at predetermined intervals of time, for processing said plurality of oxygen sensor output signals, and for determining an estimate of said output parameter of interest based upon said oxygen sensor output signals and said known transfer function; and means for outputting an indication of said estimate of said output parameter of interest.

4. A method for determining a dynamically changing output parameter of interest within a patient ventilation system, the method comprising the steps of:

providing an oxygen sensor exhibiting a dynamic characteristic having a time constant, resulting in a transient performance of the oxygen sensor, said oxygen sensor having a known transfer function;

generating oxygen sensor output signals from said oxygen sensor;

determining an estimation of said output parameter of interest based upon said known transfer function and a plurality of said oxygen sensor output signals at predetermined intervals of time; and outputting an indication of said estimation of said output parameter of interest.

5. In a system for determining a dynamically changing output parameter of interest in a patient ventilation system, said patient ventilation system having a source of breathing gas and a ventilation flow path for delivering said breathing gas, comprising:

an oxygen sensor for generating oxygen sensor output signals for determining the output parameter of interest of said breathing gas in said ventilation flow path, said oxygen sensor exhibiting a dynamic characteristic having a time constant, resulting in a transient performance of the oxygen sensor, and said oxygen sensor having a known transfer function;

computing means connected to said oxygen sensor for receiving said oxygen sensor output signals at predetermined intervals of time, for processing a plurality of said oxygen sensor output signals, and for determining an estimate of said output parameter of interest of said breathing gas in said ventilation flow path based upon said oxygen sensor output signals and said known transfer function; and means for outputting an indication of said estimate of said output parameter of interest of said breathing gas in said ventilation flow path.

6. A method for determining a dynamically changing output parameter of interest in a patient ventilation system, the steps of the method comprising:

providing a ventilator having a source of breathing gas and a ventilation flow path for delivering said breathing gas;

providing an oxygen sensor exhibiting a dynamic characteristic having a time constant, resulting in a transient performance of the oxygen sensor, said oxygen sensor generating oxygen sensor output signals and having a known transfer function for determining the output parameter of the breathing gas in the ventilation flow path;

determining an estimation of said output parameter of interest of said breathing gas in said ventilation flow path based upon said oxygen sensor output signals and said known transfer function; and outputting an indication of said estimation of said output parameter of interest of said breathing gas in said ventilation flow path.

* * * * *